United States Patent
Iddan et al.

(10) Patent No.: US 9,788,883 B2
(45) Date of Patent: Oct. 17, 2017

(54) METHOD AND APPARATUS FOR IN-VIVO CAUTERIZATION OF LESIONS AND MALIGNANCIES

(71) Applicant: GIVEN IMAGING LTD., Yoqneam (IL)

(72) Inventors: Gavriel J. Iddan, Haifa (IL); Zvika Gilad, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 5 days.

(21) Appl. No.: 14/400,117

(22) PCT Filed: May 9, 2013

(86) PCT No.: PCT/IL2013/050399
§ 371 (c)(1),
(2) Date: Nov. 10, 2014

(87) PCT Pub. No.: WO2013/168163
PCT Pub. Date: Nov. 14, 2013

(65) Prior Publication Data
US 2015/0141750 A1    May 21, 2015

Related U.S. Application Data

(60) Provisional application No. 61/645,259, filed on May 10, 2012.

(51) Int. Cl.
*A61B 1/00*    (2006.01)
*A61B 1/04*    (2006.01)
(Continued)

(52) U.S. Cl.
CPC ........ *A61B 18/082* (2013.01); *A61B 1/00029* (2013.01); *A61B 1/00087* (2013.01);
(Continued)

(58) Field of Classification Search
CPC ....... A61B 18/082; A61B 19/20; A61B 1/041; A61B 1/06; A61B 1/00158
(Continued)

(56) References Cited

U.S. PATENT DOCUMENTS 5,993,378 A    11/1999  Lemelson
7,894,882 B2    2/2011  Mullick et al.
(Continued)

FOREIGN PATENT DOCUMENTS

| JP | 04-022325 | 1/1992 | |
| WO | WO-2010093042 A1 * | 8/2010 | ......... A61B 1/00082 |
| WO | WO 2012/090197 | 7/2012 | |

OTHER PUBLICATIONS

International Search Report for International Application No. PCT/IL2013/050399, mailed Aug. 8, 2013.

*Primary Examiner* — Timothy J Neal
(74) *Attorney, Agent, or Firm* — Pearl Cohen Zedek Latzer Baratz LLP (57) ABSTRACT

An in vivo capsule has a cauterization element that may be deployed by physician while in vivo for cauterizing a lesion, such as bleeding. Energy is transferred from outside of the patient's body to the capsule and specifically to the ablating element, such as via a resonance circuit. Accordingly, it is the object of the present invention to provide a method and apparatus for precisely cauterizing or ablating tissue in-vivo. Embodiments of the invention may provide an in-vivo device having a cauterization or ablation element incorporated therein and a system and method for controlled navigation of the in-vivo cauterization device through a body lumen.

10 Claims, 4 Drawing Sheets

(51) Int. Cl.
    *A61B 18/08*     (2006.01)
    *A61B 1/06*     (2006.01)
    *A61B 90/10*     (2016.01)
    *A61B 34/00*     (2016.01)
    *A61B 17/00*     (2006.01)
    *A61B 18/00*     (2006.01)
    *A61B 90/30*     (2016.01)
    *A61B 90/00*     (2016.01)

(52) U.S. Cl.
    CPC .......... *A61B 1/00158* (2013.01); *A61B 1/041* (2013.01); *A61B 1/06* (2013.01); *A61B 18/08* (2013.01); *A61B 34/72* (2016.02); *A61B 34/73* (2016.02); *A61B 90/10* (2016.02); *A61B 90/37* (2016.02); *A61B 2017/00278* (2013.01); *A61B 2017/00411* (2013.01); *A61B 2017/00876* (2013.01); *A61B 2018/00184* (2013.01); *A61B 2018/00595* (2013.01); *A61B 2018/00982* (2013.01); *A61B 2034/731* (2016.02); *A61B 2090/309* (2016.02)

(58) Field of Classification Search
    USPC ........................................................ 600/104
    See application file for complete search history.

(56) References Cited

U.S. PATENT DOCUMENTS

| | | |
|---|---|---|
| 2002/0198470 A1 | 12/2002 | Imran et al. |
| 2009/0299359 A1 | 12/2009 | Swain |
| 2009/0299362 A1 | 12/2009 | Long et al. |
| 2011/0065987 A1 | 3/2011 | Mullick et al. |
| 2011/0166416 A1 | 7/2011 | Katayama et al. |
| 2011/0301497 A1 | 12/2011 | Shachar et al. |

\* cited by examiner

METHOD AND APPARATUS FOR IN-VIVO CAUTERIZATION OF LESIONS AND MALIGNANCIES

CROSS-REFERENCE TO RELATED APPLICATIONS

This application is a National Phase Application of PCT International Application No. PCT/IL2013/050399, International Filing Date May 9, 2013, claiming priority of U.S. Provisional Patent Application No. 61/645,259, filed May 10, 2012, which is hereby incorporated by reference.

FIELD OF THE INVENTION

The present invention relates to devices and methods for cauterization of lesions and malignancies in-vivo using a capsule in-vivo device.

BACKGROUND OF THE INVENTION

The medical practice or technique of cauterization is the use of heat to destroy tissue or close bleeding blood vessels in an attempt to mitigate damage, remove an undesired growth, or minimize other medically harmful possibilities, such as infections.

The cauterization of a source of bleeding is one of the most frequently required therapeutic treatments performed in the gastrointestinal (GI) tract. However, cauterization at a specific location can be difficult to achieve using traditional endoscopes because traditional endoscopes may not be capable of reaching the desired location within the GI tract, as a traditional endoscope can be difficult to maneuver so as to aim the cauterization element with any degree of precision. In addition, traditional endoscopes may not be capable of reaching a desired location that is located within approximately the last two thirds of the small bowel, since traditional endoscopes are limited in their length and maneuverability.

Capsule endoscopes may be used to cure some of these deficiencies. However, even capsule endoscopes can be difficult to control and aim at a specific location. Additionally, internal power sources contained within a capsule may be inadequate to activate a cauterization element so that it has sufficient heat for cauterization.

SUMMARY OF THE INVENTION

Accordingly, it is the object of the present invention to provide a method and apparatus for precisely cauterizing or ablating tissue in-vivo.

Embodiments of the invention may provide an in-vivo device (e.g., a swallowable capsule) having a cauterization or ablation element incorporated therein and a system and method for controlled navigation of the in-vivo cauterization device through a body lumen and for application of the cauterization or ablation element at a desired location.

In certain embodiments of the invention, the in-vivo device has a cauterization or ablation element that may be aimed at a tissue in need of cauterization or ablation in-vivo. The cauterization element may be installed on or in the in-vivo imaging device for cauterizing a tissue (e.g., a lesion, polyp, tumor, etc.) located within a body lumen in-vivo and may be movably mounted to the in-vivo device so as to be extendable or expandable (i.e., lengthened or pushed-out) and retractable relative to the in-vivo imaging device. The cauterization element may be stored within or on the in-vivo imaging device until needed, extended or expanded from the in-vivo imaging device towards the tissue to be cauterized, and then retracted or withdrawn once the cauterization is complete.

In certain embodiments, the cauterization element is manufactured from an alloy having a high resistance to electrical conductivity, although other types of alloys, metals or materials may be used. In certain embodiments the cauterization element is manufactured from Nichrome or other stainless steel. The system may include external induction coils for externally activating the cauterization element in-vivo.

In certain embodiments of the invention, the in-vivo device has an imager for imaging the body lumen in-vivo. In certain embodiments, the imager is in line with the cauterization element stored on or in the in-vivo device. That is, the imager's field of view is centered on the cauterization element so that the cauterization element can be effectively aimed at a specific site within the imager's field of view and extended to cauterize tissue at that specific site. In other embodiments, the imager's field of view is not necessarily centered on the cauterization element. In some embodiments, the device may comprise a dome. In such embodiments, the cauterization or heating element may be shaped such as to conform to the curvature of the in-vivo device's dome.

In certain embodiments of the invention, cauterization or ablation element may be aimed at a tissue in need of cauterization or ablation in-vivo, and extended (i.e., expanded, lengthened or pushed-out) from the in-vivo device until the cauterization element touches the tissue, and then activated so as to cauterize the tissue in-vivo. In certain embodiments, the cauterization element may be activated internally by a power source located within the in-vivo device. In other embodiments, the cauterization element may be activated by an external source of energy. For example, in certain embodiments, the cauterization element is activated by induction coils located externally to the patient's body. In certain embodiments, the external transfer of energy may be carried out in an efficient way by having the cauterization element as part of the resonance circuit.

In certain embodiments, the process of application of the cauterization element at a desired location involves supplying energy to the power source within the in-vivo device, extending the cauterization or ablation element from the in-vivo device against the tissue to be cauterized, transferring energy from the power source within the in-vivo device to the cauterization or ablation element, stopping the transfer of energy to the cauterization or ablation element, and withdrawing the cauterization or ablation element back into the in-vivo device.

According to embodiments of the invention, a system for cauterizing tissue in-vivo may include an in-vivo imaging device (e.g., a swallowable capsule), such as described above, comprising a cauterization or ablation element, an imager, a pressure sensor and a transmitter. The pressure sensor may produce pressure data representative of forces acting on the in-vivo imaging device in-vivo. The system may further include a receiver to receive in-vivo image data, pressure data and other data, which may be produced in the in-vivo imaging device.

The system may also include means for controlled navigation of the in-vivo cauterization device through a body lumen and for application of the cauterization element at a desired location. In certain embodiments, the controlled navigation of the in-vivo device involves means for propelling the in-vivo device through the body lumen, means for stopping the in-vivo device at a specific location within the body lumen, means for changing the orientation (e.g., twisting, turning, rotating, raising, lowering and/or angling) of the in-vivo device while in-vivo, and means for maintaining the in-vivo device at said in-vivo location and in said orientation for a specified period of time. In certain embodiments of the invention, maintaining the in-vivo device at said location and in said orientation may be considered for aiming the in-vivo device in a specific direction or at a specific target.

An in-vivo imaging device positioning unit may indicate the current position of the in-vivo imaging device within the three-dimensional space of the imaging system, and produce corresponding (i.e., current) position data. External magnets may be used to generate a driving force to navigate the in-vivo imaging device according to a calculated target direction vector, and the external magnets may be used to control the orientation of the in-vivo imaging device so as to point or aim the in-vivo imaging device in a specific direction or at a precise location in-vivo. The external magnets may also be used, for example, to locally scan the body lumen by the in-vivo imaging device by causing a predetermined motion pattern of the in-vivo imaging device within a region proximate to its current position. The system may include a processor to calculate a target direction vector for navigating the in-vivo imaging device based on image processing, and/or based on the direction producing a minimal pressure force on the in-vivo imaging capsule, which may have been sensed during the local scan.

According to some embodiments, the in-vivo imaging device positioning system may include internal coils in the in-vivo imaging capsule, gravity sensors or accelerometers. The system may include fiduciary elements, which may be placed on or attached to the patient or on a fixed component or reference point in the system such as the operation table (e.g., bed), on the floor, etc.

According to some embodiments, a method is provided for cauterizing a tissue in a body lumen of a patient in-vivo. The method may include receiving, substantially in real-time, an in-vivo image of the body lumen captured by the in-vivo imaging device, analyzing the in-vivo image to identify a tissue in need of cauterization and cauterizing the identified tissue. The method may include maneuvering the in-vivo imaging device through the body lumen of the patient, e.g., magnetically, to the location of a tissue in need of cauterization, and then maintaining, or aiming, the in-vivo imaging device at said location and cauterizing said tissue. The method may include activating a cauterization element from a position external to the patient's body such as with, for example, external induction coils. In certain embodiments, the method may include storing the cauterization element on or in the in-vivo imaging device, extending, lengthening or expanding the cauterization element towards the tissue to be cauterized, cauterizing the tissue in-vivo, and retracting, withdrawing, or repealing the cauterization element.

In certain embodiments of the invention, the in-vivo device is controllably navigated by magnetically maneuverable capsule endoscopes such as those described, for example, in PCT International Patent Application No. PCT/IL2011/000972, filed Dec. 29, 2011, which is commonly owned by the assignee of the present application and is incorporated herein by reference in its entirety.

A method for magnetically maneuvering an in-vivo imaging device (e.g., a capsule endoscope) in-vivo may include, for example, receiving in-vivo images of the body lumen from the in-vivo imaging device, and receiving current position data of the imaging device. In some cases, for example, if the images are clear and provide a detectable view of the lumen opening or the direction of the tissue wrinkles, a target direction vector may be calculated based on the received images. If no target direction vector may be calculated due to turbid, unclear images, or images which depict a close view of the tissue walls instead of the tissue lumen opening, a local scan of the body lumen may be generated, for example, by inducing a predetermined motion pattern of the imaging capsule within a region proximate to its current position.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those of ordinary skill in the art that the present invention may be practiced without these specific details. In other instances, well-known methods, procedures, components and circuits have not been described in detail so as not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise controllers, computers or processors selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus. It will be appreciated that a variety of programming languages may be used to implement the teachings of the invention as described herein.

Embodiments of the invention may include an article such as a computer or processor readable medium, or a computer or processor storage medium, such as for example a memory, a disk drive, or a USB flash memory, encoding, including or storing instructions, e.g., computer-executable instructions, which when executed by a processor or controller, carry out methods disclosed herein.

Some embodiments of the present invention are directed to a typically swallowable in-vivo device/capsule, such as an autonomous swallowable capsule. In other embodiments, the in-vivo device need not be swallowable or autonomous, and may have other shapes or configurations.

Figure 1:
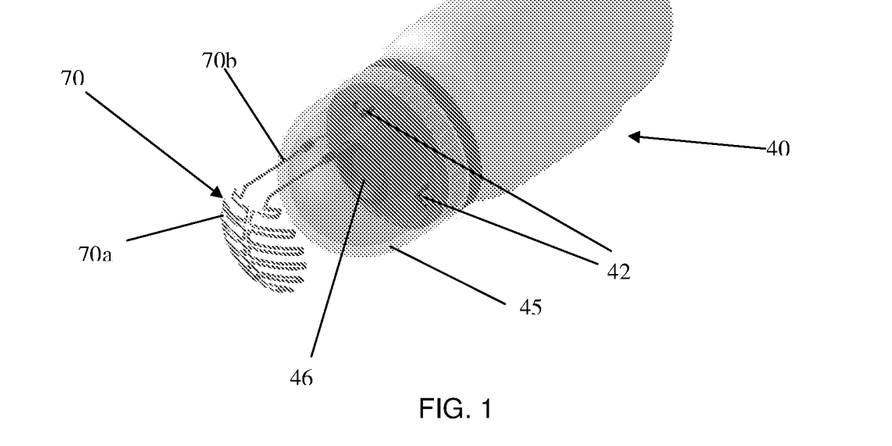
FIG. 1 is an illustration of an in-vivo imaging and cauterization device.
Figure 2:
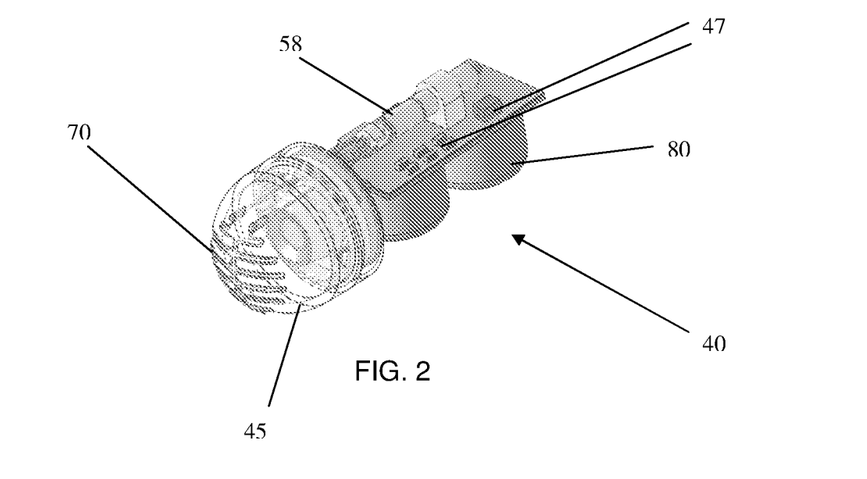
FIG. 2 is an illustration of an in-vivo imaging and cauterization device, with its outer housing removed.

Reference is made to FIGS. 1 and 2, which show illustrations of an in-vivo imaging and cauterization device 40 according to embodiments of the invention. According to some embodiments, device 40 may include at least one illumination source 42 for illuminating the body lumen, an optical head 46 comprising an imager for capturing images of the body lumen, and an optical system (which may comprise lenses or mirrors, or a dome 45) used to focus reflected light onto the imager, and an electronic circuitry and transmitter 47 to control the capsule functionalities such as transmitting image data and additional data to an external data receiver.

The imager, which is part of optical head 46 may be a suitable complementary metal-oxide-semiconductor (CMOS) camera, such as a "camera on a chip" type CMOS imager specified by Given Imaging Ltd. of Israel and designed by Micron Technology, Inc. In alternate embodiments, the imager may be another device, for example, a charge-coupled device (CCD). Illumination source 42 may be, for example, one or more light emitting diodes, or another suitable light source, as is known in the art. In some embodiments, optical head 46 and illumination source 42 may be covered by dome 45 such that optical head 46 and illumination source 42 may be located behind the concave side of dome 45.

Electronic circuitry and transmitter 47 may include, for example, an input-output ("I/O") interface/device, one or more controllers and a receiver. The receiver may be used, for example, to receive control information (e.g., to change a mode of operation, to change the value of a parameter, etc.) and various messages.

Device 40 may include a heating element 70, which may be located at a terminal end of device 40 as shown in FIGS. 1 and 2, although the heating element 70 may be located at other positions on or in device 40. Heating element 70 may be positioned at the same terminal end of device 40 as the position of optical head 46. In certain embodiments of the invention, heating element 70 may be a single piece of elongated wire that has an elongated, straight proximal portion 70b and a bent and/or twisted, distal portion 70a having a substantially flat surface. The distal portion 70a of heating element 70 may have a plurality of fork-like tines, prongs or twists that enable it to have better contact with a larger surface area of tissue for cauterization of tissue in-vivo. In alternative embodiments, heating element 70 may have other shapes such as, for example, plate, saucer, needle or pin shaped.

Heating element 70 may be typically made of inert metal such that heating element 70 would not be oxygenated and would be stable during passage of heat through it. For example, heating element 70 may be made of Nichrome, though other materials may be used, typically selected from stainless steel metals. In embodiments where heating element 70 is an elongated wire, the diameter of the wire may, for example, be less than 1 mm before activation of heating element 70. In embodiments where heating element 70 is in the shape of a needle, the needle may be used to inject various fluids, e.g., medications, in addition to it being used to cauterize the tissue.

According to embodiments of the invention, device 40 may have a cylindrical shape, an egg shape, a ball shape or any other round-type shape so as not to create any sharp edges at one terminal end. In certain embodiments, heating element 70 may be compactly stored inside, on or against device 40. In other embodiments, when not in use, heating element 70 may be adapted to rest on the surface of device 40, such as, for example, heating element 70 may be shaped so as to conform to the curvature of dome 45 of device 40 (see FIG. 2). When heating element 70 is stored inside, on or against device 40, device 40 does not become stuck or trapped within the body lumen due to entanglement of body tissue with heating element 70 and is allowed to progress smoothly through the body lumen, whether by external maneuvering or by natural peristalsis.

Heating element 70 may be extendable or expandable from device 40. For example, heating element 70 may be stored against, on or in device 40 until device 40 reaches a desired location in-vivo. At the desired location, heating element 70 may be extended from its stored position towards a tissue that is to be cauterized until it comes into contact with said tissue. Heating element 70 would then be activated, wherein it is heated up to cauterize the tissue. Following cauterization, heating element 70 would then be retracted back to its stored position, to allow device 40 to continue its progression through the body lumen (e.g., GI tract). Extending or expanding heating element 70 away from the body of device 40 helps protect the components of device 40, such as dome 45, from heat damage during the cauterization process. The distance between heating element 70 and dome 45 during activation of heating element 70 should be more than 3 mm.

In one embodiment, as shown in FIG. 2, device 40 may have a mechanism that moves heating element 70 outward, away from device 40 and inward, towards device 40 via movement of elongated, straight proximal portion 70b, such as a micro-motor 58. Micro-motor 58 grips elongated, straight proximal portion 70b of heating element 70, and, under control of an external controller, moves elongated proximal portion 70b of heating element 70 the desired distance and for the desired time period. Other armatures or motors can be suitably designed. An example for micro-motor 58 may be micro-motors as manufactured by NAMIKI PRECISION JEWEL CO. LTD, Japan.

Device 40 may be a swallowable in-vivo capsule, but other sorts of devices or suitable implementations may be used. In an example embodiment, device 40 may communicate with an external receiving and display system to provide display of data, control capability, or other functions. Power to device 40 may be provided, for example, by an internal battery (either disposable or rechargeable), and/or by any device or circuit capable of picking up power, like coils, e.g., copper, that are responsive either to magnetic fields or to an RF transmission or any other wireless receiving system. If batteries are used, such as, for example, batteries 80 in FIG. 2, it is preferred that batteries of low resistance be used, so that they do not generate additional heat within device 40 during the cauterization procedure. Other embodiments may have other configurations and capabilities. In certain embodiments, the functional features of device 40, such as heating element 70, may require energy or power that is beyond the delivering capability of device 40 such as, for example, beyond the capabilities of one or more small internal batteries that can be compactly stored within device 40. In these embodiments, heating element 70 may be designed as part of a resonance circuit wherein an external oscillator will excite and heat up heating element 70 in-vivo (see FIG. 4), as will be further discussed below.

In certain embodiments, the field of view of the imager included in optical head 46 may be through or around heating element 70. For example, if heating element 70 is manufactured comprising a twisted distal portion 70*a* with a plurality of prongs, the imager may be able to view through spaces between the prongs, and thus cauterization element 70 may be centered within the field of view of the imager. In this embodiment, the imager may help position or aim heating element 70 towards the tissue to be cauterized, which in turn minimizes the risk of collateral damage to adjacent tissue.

Figure 3:
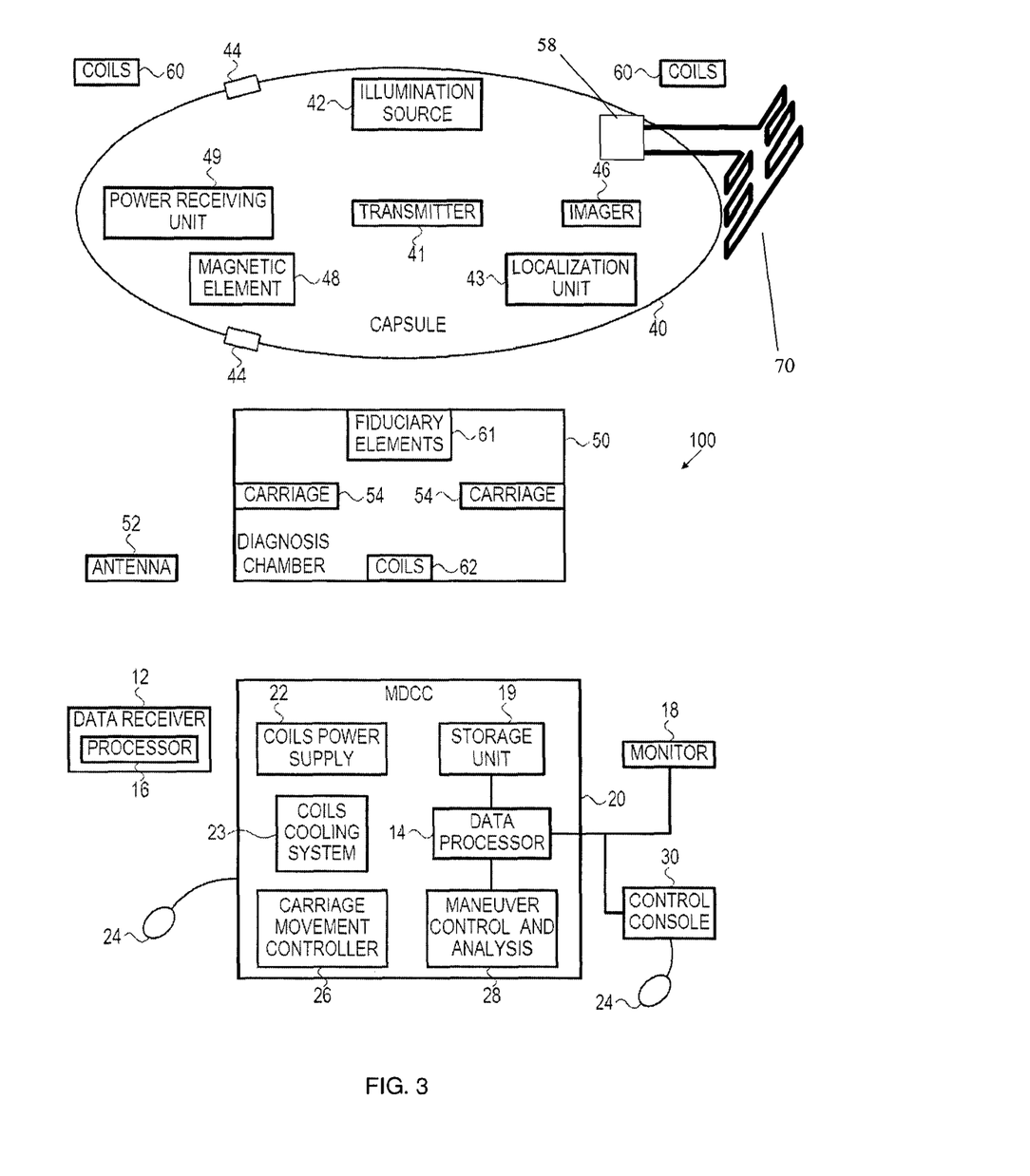
FIG. 3 is a schematic illustration of an in-vivo imaging and cauterization system.

Reference is made to FIG. 3, which shows a schematic illustration of an in-vivo imaging and cauterization system 100 according to embodiments of the invention. According to some embodiments, system 100 may comprise an in-vivo imaging device or capsule 40 as described above, a power receiving unit 49 and a capsule localization/positioning unit 43, which may include, e.g. coils, Hall Effect probes, gyro, acceleration meter, etc. Power receiving unit 22 may wirelessly receive power, for example, by 'picking up' electromagnetically energy.

Data receiver 12 preferably including a processor 16, may receive data from device 40. Processor 16 may be, for example, a DSP or any other real time processor or controller. In some embodiments, data receiver 12 may include a storage unit for storing the received data, while in other embodiments the data may not be stored in the receiver 12, and may either be transmitted or transferred to another storage unit or may not be stored at all. Processor 16 of data receiver 12 may calculate the localization parameters of device 40, and may be responsible for other communication tasks such as sending the data to a regulator of diagnosis chamber 50 and to the physician display station.

According to one embodiment of the invention, system 100 may include a control unit 20, which is referred to herein as a Medical Displays and Control Console (MDCC), for receiving the stream of images and localization data from data receiver 12, processing the images' stream and localization data and displaying the stream of images (or individual images) and the localization data (and optionally additional information) to the physician. An input device 24 may be operationally connected to MDCC 20, and may be used to receive input of destination data for capsule 40 from a user (e.g., input device 24 may be or include a joystick, a pointing device or mouse, a keyboard, touch screen, stylus, light pen, trackball, or any other input device). The input data, or a modified or processed version thereof, may be sent to the regulator of diagnosis chamber 50 in order for it to facilitate generation of maneuvering commands MDCC 20 may include a data processor 14, a storage unit 19 for storing, for example, data processed by data processor 14, and one or more monitors such as image monitor 18, which may be included as part of a personal computer or workstation which includes standard components such as a processor, a memory, a disk drive, and input-output devices, although alternate computer configurations are possible, and the system and method of the present invention may be implemented on various suitable computing systems.

Data processor 14 may include any standard data processor, such as a microprocessor, multiprocessor, accelerator board, or any other serial or parallel high performance data processor. Image monitor 18 may be a computer screen, a plurality of screens, conventional video displays, or any other device capable of providing a video stream, images and/or other data.

In operation (during the imaging process), the imager may capture images and send data representing the images (e.g., image data) to transmitter 41. At the same time, localization unit 43 may detect signals representing location, and may output corresponding localization data to transmitter 41. Transmitter 41 transmits the image data and the localization data, or localization signals representing the localization data, to data receiver 12 using, for example, electromagnetic radio waves. Data receiver 12 may transfer the image data, and optionally other types of data, to data processor 14 that may store the transferred data in storage unit 19. In parallel, data receiver 12 may also transfer the data to the regulator of diagnosis chamber 50 to allow motion control of device 40. The data (e.g., image data and localization data) collected and stored may be stored indefinitely, transferred to other locations, or manipulated or analyzed. A healthcare professional may use the images to diagnose pathological conditions of, for example, the GI tract, and, in addition, the system may provide information about the location of these pathologies. The data may be analyzed and used as input for the maneuver control and analysis unit 28.

According to one embodiment, still images transmitted from device 40 as it traverses the GI tract may be combined consecutively to form a moving image stream and transmitted, sent or otherwise communicated to image monitor 18, which may either be connected to data processor 14 or remotely located in a central review station, where a healthcare professional may view the images as a live or real time movie. In this embodiment, the healthcare professional viewing the images in real time may be able to identify a tissue in need of cauterization while device 40 traverses the GI tract. Using the maneuvering capabilities of device 40 described hereinbelow, the healthcare professional may then be able to halt device 40 and change its orientation so that heating element 70 is aimed at the tissue to be cauterized. The heating element 70 could then be extended towards the tissue to be cauterized and activated so that cauterization may take place. The maneuvering capabilities of device 40 as described hereinbelow may help maintain device 40 at a certain location and in a certain orientation so that cauterization could safely occur.

Data processor 14 may analyze and edit the data, storage unit 19 may store raw data and/or processed data, and may provide the analyzed and edited data to, for example, a healthcare professional at a later time.

Device 40 may record images at a rate of, for example, two to forty images per second, though other rates may be used. Device 40 may have a fixed or variable frame capture rate and/or transmission rate, fixed or variable field of view, and fixed or variable image magnification which may be changed automatically or by a command from a user. When the imager has a variable or adaptive frame rate (AFR) capability, the imager may switch back and forth between frame rates, for example, based on parameters, such as device 40 speed, estimated location, similarity between consecutive images, or other criteria. Alternatively, the user (e.g., healthcare professional) may choose when to increase or decrease the image frame rate. For example, the healthcare professional may want to decrease the image frame rate as device 40 traverses the body lumen, but may want to increase the image frame rate when a tissue to be cauterized is identified and the healthcare professional is attempting to aim heating element 70 of device 40 at the tissue. The image recordation rate, the frame capture rate, the total number of images captured, the total number of images selected for the edited moving image, and the view time of the edited moving image, may each be fixed or varied.

Preferably, the image data recorded and transmitted by device 40 is digital color image data, although in alternate embodiments other image formats may be used. In an exemplary embodiment, each frame of image data includes 256 rows of 256 pixels each, and each pixel may have associated with it binary bytes for quantifying the pixel's color and brightness, according to known methods. Other numbers of pixels may be used, for example 320×320 pixels may be captured in an image frame, or high definition video resolution may be used, e.g., 1,280×720 pixels. For example, in each pixel, color may be represented by a mosaic of four sub-pixels, each sub-pixel corresponding to primary colors such as red, green, or blue (where one primary color is represented twice). In alternate embodiments, other formats such as hyper-spectral with multiple color filters may be used. The brightness of the overall pixel may be recorded by a one byte (i.e., 0-255) brightness value. According to one embodiment, images may be stored sequentially in data processor storage unit 19. The stored data may include one or more pixel properties, including color and brightness.

While, preferably, information gathering, storage and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle, etc.

According to an embodiment of the invention, system 100 also has a maneuver regulator (e.g., maneuver control and analysis unit 28). Maneuvering regulator 28 may be a Programmable Logic Controller (PLC) or any other suitable commercial regulator known in the art. Maneuver control and analysis unit 28 may be a Modular PLC Controller, which may include discreet input and output modules, a module for monitoring a cooling system 23, a thermocouple module for coil temperature monitoring, dedicated modules for power monitoring, etc.

Maneuvering regulator 28, an example maneuver control and analysis unit, may receive input data, such as localization information detected by localization unit 43, and commands from control console 30, and generate/output, based on the input data and using dedicated algorithms, electrical current commands for coils 60 that surround device 40 for producing magnetic fields for driving device 40 within the GI tract.

Figure 4:
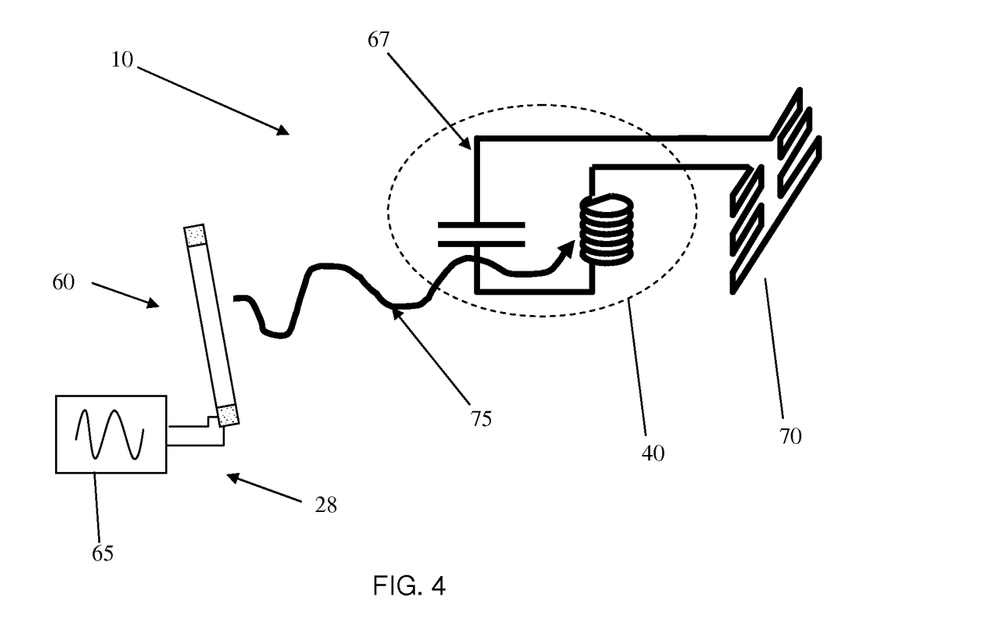
FIG. 4 is a schematic illustration of an in-vivo imaging and cauterization system, showing the energy transfer from induction coil and oscillator to a resonance circuit and heating element of the in-vivo device.
Figure 5:
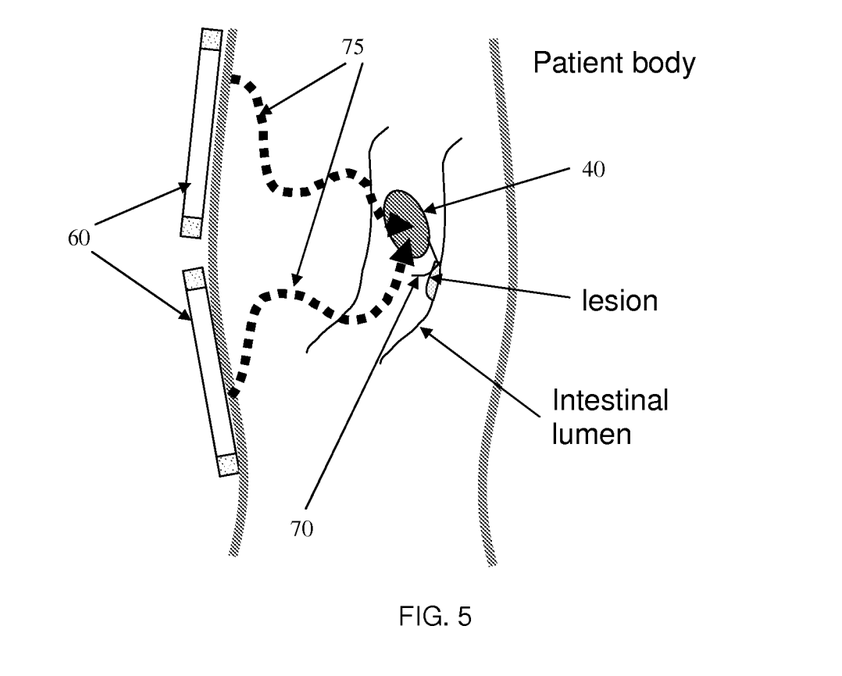
FIG. 5 is a schematic illustration of an in-vivo imaging and cauterization system, showing the in-vivo device within the GI tract of a patient and induction coils external to the patient.

In certain embodiments of system 100, device 40 may be surrounded by external magnetic field generators, e.g., induction coils 60, as shown in FIGS. 4 and 5. Coils 60 may induce controlled and regulated magnetic fields 75, for example as per the electrical current commands output/generated by maneuvering regulator 28. The magnetic fields 75 generated by induction coils 60 may interact with magnetic elements 48 to produce controlled translation and torque forces for moving, rotating and orienting device 40.

Moreover, the arrangement as described herein provides the forces and rotational torques not only to be exerted on the internal magnetic and conductive elements of a vessel such as the capsule to move, tilt and rotate in the body lumens, but also to follow, for example, an operator's or automatic computer generated direction and orientation commands. According to some embodiments, the external magnetic fields need to overcome a force in the range of, for example, 10 grams or 100 grams.

Pressure forces acting on the in-vivo imaging capsule during the local scan may be sensed, for example using pressure sensors located on a housing surrounding the in-vivo device. A target direction vector for navigating the in-vivo imaging capsule may be determined, for example by determining the direction which induces the minimal pressure force on the capsule as sensed during the local scan. A driving force to navigate the imaging capsule in the determined direction vector may be generated, for example by using external magnets which create an external magnetic field.

According to some embodiments, pressure sensors may be installed in device 40, in order to provide information regarding the pressure that the capsule exerts on a wall of a body lumen. In an alternative or a complementary embodiment, measurement of the pressure exerted by the capsule on a tissue of a wall of a body lumen may be deducted from the movement of the capsule when the resistance to the movement (if the capsule is driven into the tissue) is detected by the location system. For example if a certain amount of force is expected to move the capsule two centimeters (cm) away but the capsule actually moved only 1 cm, it may indicate unexpected resistance and thus may be interpreted as a movement of the capsule into a lumen wall or as the movement having a vector component directed towards the lumen wall.

In some embodiments, the local scan may include generating a conical magnetic driving force, which may initiate a conical motion pattern of the in-vivo imaging capsule in the body lumen. For example, the conical magnetic driving force may be generated by generating a forward driving magnetic field and at least two orthogonal harmonic magnetic fields. In some embodiments, sensing pressure forces acting on the in-vivo imaging capsule may include calculating the difference between an expected spatial positioning of the capsule as a result of the forces generated in the local scan motion and an actual spatial positioning of the capsule determined by a capsule positioning unit.

Relative position information of the imaging capsule in the three-dimensional operating space may be received, for example from fiduciary elements which may be positioned on the patient's body and/or on the operating table or bed on which the patient is lying during the imaging procedure. The rotation and translation of the in-vivo imaging capsule may be calculated, for example based on the capsule positioning information received from the position/localization unit, and/or on the relative position information received from the fiduciary elements.

In some embodiments, when no target direction vector may be calculated using one or more methods, the external magnetic fields may be shut down or substantially lowered, in order to allow the in-vivo device to naturally resume the correct direction and orientation for proceeding through the body lumen.

In one embodiment, as shown in FIG. 3, one or more pressure sensors 44 may be positioned on the housing of device 40, for example creating a structure similar to a ring near the capsule dome. Pressure sensors 44 may be located on the front of device 40, or on another part of the capsule in order to detect occurrences of high pressure acting on the device 40 during the medical examination, and/or to detect peristaltic waves and provide input to maneuvering regulator 28 to increase counter forces to reduce such pressures. Such pressure sensors may be similar to, for example, General Electric's P161 sensor, which is a miniature silicon piezoresistive pressure sensor die.

In certain embodiments, as shown in FIG. 3, system 100 may comprise a patient diagnosis chamber 50, which may include an array of electromagnets (source coils 62) arranged around a subject's torso on a standard patient table or carriages 54. Carriages 54 may be installed on rails located on or next to diagnosis chamber 50 and may slide in and out of diagnosis chamber 50. In some embodiments, carriages 54 may be fixed, and may enable diagnosis chamber 50 to slide along them. Diagnosis chamber 50 may also include an antenna or antenna array (antenna 52) to facilitate communication between capsule 40 and a data receiver 12, using a wireless communication such as radio frequency ("RF") communication, acoustic waves and/or ultrasound based communication. Antenna or antenna array 52 may be placed at various locations around chamber 50 or may be embedded within or below carriage 54.

According to a preferred embodiment, fiduciary elements 61 are attached to the subject to be examined, the subject lies on carriages 54 and his/her set of position coordinates relative to the bed is measured and used to calibrate the diagnosis chamber 50. Such setup/preparation procedure may take a short time, for example less than one minute. A device or capsule 40 may be inserted into, or swallowed by the patient. The maneuvering magnetic fields 75 are then activated and the capsule navigation may commence. A patient is expected to undergo the medical imaging procedure for a time period ranging from, for example, a few minutes for a short screening procedure (e.g., upper GI exam) up to two hours for a more lengthy GI tract examination. Typically, the system may work continuously during the day. Overlap may be possible, for example in the workstation level, for example during a current examination or imaging session, the results, or outcome, of a previous examination, or imaging session, may be handled (e.g., reviewed, further processed, stored or archived on the workstation or on another networked station).

According to embodiments of the present invention, a physician may view real-time movie images transmitted by the capsule endoscope in virtually real time, may watch the viewed organ or tissue concurrently from several perspectives, viewpoints and angles, and, optionally, use the visual feedback to navigate the capsule to a desired location, to position it in a desired orientation and to stop it—as may be needed for, for example, cauterization or ablation using heating element 70.

Reference is now made to FIG. 5, which is a diagrammatic illustration of an in-vivo imaging and cauterization device within the GI tract, including induction coils 60 and heating element 70 protruding from the in-vivo device 40 according to an example embodiment of the invention. In FIG. 5, for example, device 40 has been navigated to a location of a tissue in need of cauterization or ablation. Using the imager included in optical head 46, device 40 and heating element 70 have been aimed or directed at the tissue, and heating or cauterization element 70 is extended from device 40 until heating element 70 comes into contact with the tissue. The position of device 40 is maintained by the externally applied magnetic field 75. After coming into contact with the tissue, heating element 70 is activated in-vivo by induction coils 60 positioned externally to the patient's body. Once cauterization or ablation is complete, heating element 70 is deactivated and retracted by into or onto capsule 40, and capsule 40 may continue through the body lumen.

In certain embodiments of the invention, induction coils 60 may also operate to provide power to the in-vivo device 40. For example, induction coils 60 may provide power external to in-vivo device 40 to power the imager and to expand and retract heating element 70. For example, power receiving unit 49 and heating element 70 may form parts of a single circuit within capsule 40, but it may be an open circuit in that heating element 70 may not be activated until a switch is flipped to close the circuit. When heating element 70 is ready to be activated, a user, or healthcare professional, may activate the switch to close the circuit thereby activating and heating cauterization element 70.

Reference is made to FIG. 4 which is a schematic illustration of the energy transfer from induction coil 60 and oscillator 65 to a resonance circuit 67 and heating or cauterization element 70 of device 40 according to an embodiment of the invention. In certain embodiments, the power receiving unit 49 (not shown in FIG. 4) is manufactured from a coil having a low resistance to electrical conductivity such as, for example, copper wire. Heating element 70 may be manufactured from a coil having a high resistance to electrical conductivity such as, for example, Nichrome or stainless-steel. Induction coils 60 may produce a magnetic field via oscillator 65, which would in turn cause an electric current to pass through the coil of power receiving unit 49 (not shown in FIG. 4) and power the components of in-vivo device 40.

Under Ohm's Law, because the resistance of heating element 70 is high, the power supplied to it would also be high. However, because copper has low resistance, the coil would not be warmed up as compared to heating element 70. In other embodiments, power receiving unit 49 may not be a coil, but may be a battery or other type of suitable power generator. In such embodiments, the batteries should have a low resistance so as to not heat up during the procedure. The ratio between resistance of Nichrome and copper is around 100: $R_{(Nichrome)}=1*10^{-6}$; $R_{(copper)}=0.0167*10^{-6}$. A similar ratio should be kept when using batteries (either disposable or rechargeable).

Power receiving unit 49 (not shown in FIG. 4) and heating element 70 may be connected by an open circuit, such as for example, resonance circuit 67. Upon activating heating element 70, the open resonance circuit 67 is closed, and the induced electrical current would pass through heating element 70 and be converted into heat energy due to the high resistance of heating element 40. Upon deactivating heating element 70, the resonance circuit 67 is opened, and heating element 70 is allowed to cool.

In certain embodiments, resonance circuit 67 may have, for example, a resonance frequency $f_1$. When an external coil, such as, for example, induction coil 60, is energized at frequency $f_1$ by an external oscillator 65, induction coil 60 will excite resonance circuit 67 of capsule 40 and heat up cauterization element 70 via Joule heating. In certain embodiments, in order to make the transfer process more efficient, a plurality of coils, such as, for example, induction coils 60 may be deployed around a patient's body wherein each coil 60 is energized in proper phasing to generate a Huygens wave front converging on capsule 40. In this embodiment, the proper phasing may be obtained from the RF transmission from capsule 40 as it is captured by antennas.

Figure 6:
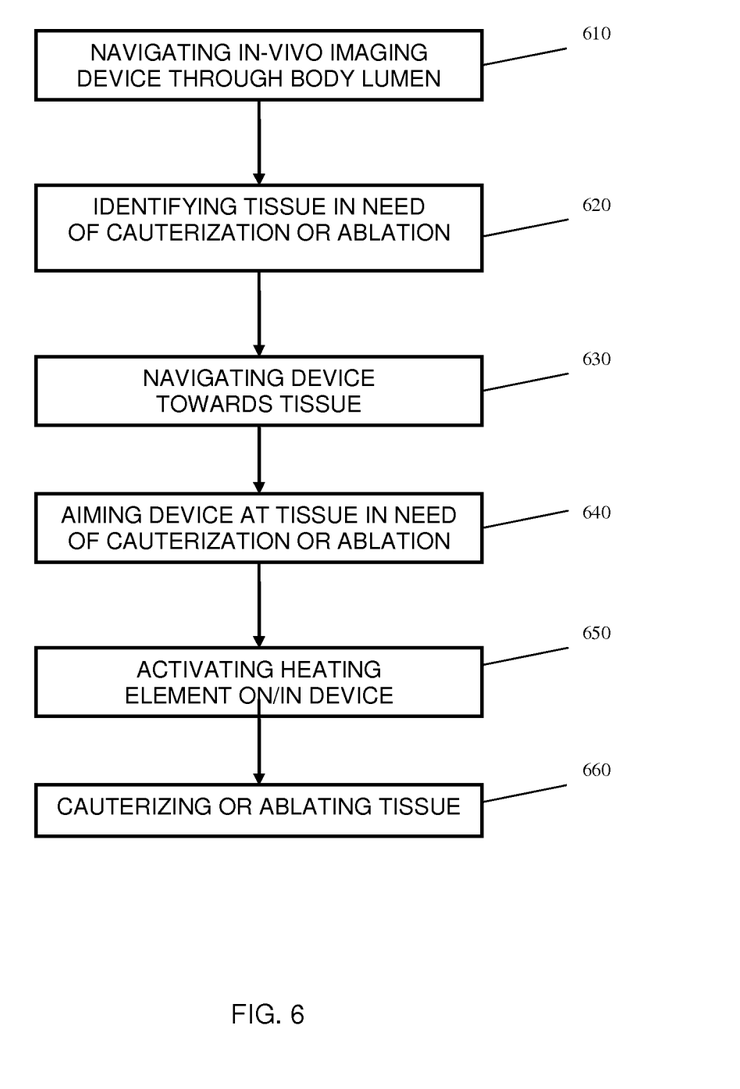
FIG. 6 is a flow chart of a method for cauterizing tissue in-vivo using the magnetically maneuverable capsule according to an example embodiment of the present invention.

Reference is now made to FIG. 6 which is a flow chart of a method for cauterizing tissue in-vivo using the magnetically maneuverable capsule according to an example embodiment of the present invention. According to some embodiments, the user (e.g., the physician) may control the capsule by selecting a direction for driving the capsule, and selecting the capsule's orientation in-vivo. If an area of interest is detected in a particular image, either automatically by image processing detectors or visually by the user, the user may mark the area of interest in the image and control the capsule to navigate or guide the capsule towards that area. For example, based on live images captured by device 40, the healthcare professional may identify a tissue in need of cauterization and may navigate device 40 to that location. In certain embodiments, the method may include the steps of, for example, navigating device 40 through a body lumen (e.g., step 610), identifying, via live image feeds from device 40, a tissue in need of cauterization or ablation (e.g., step 620), navigating device 40 towards said tissue (e.g., step 630), aiming heating element 70 at the tissue in need of cauterization or ablation (e.g., step 640), activating heating element 70 (e.g., step 650) and cauterizing or ablating said tissue (e.g., step 660). Aiming heating element 70, such as in, for example step 640, may include imaging the tissue through or around heating element 70 by the imager such that cauterization or ablation may be precisely performed. The method may further include storing heating element 70 on or in device 40, expanding or extending heating element 70 towards the tissue to be cauterized before cauterization, and retracting heating element 70 back into or onto device 40 after completion of cauterization. In certain embodiments, navigating device 40, such as in, for example, steps 610 and 630, is performed by magnetically maneuvering device 40 in-vivo by applying a magnetic field. In certain embodiments, the magnetic field is applied externally to the patient's body. In certain embodiments, activating heating element 70, such as in, for example, step 650, may include inducing an electric current to heat up heating element 70. The method may further include switching a resonance circuit in device 40 from open to closed in order to activate heating element 70.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall with the true spirit of the invention.

The invention claimed is:

1. An in-vivo device for performing in-vivo cauterization of a tissue within a body lumen, the device comprising:
   at least one illumination source for illuminating the body lumen;
   an optical head comprising: an imager for capturing images of the body lumen, and an optical system used to focus reflected light onto the imager;
   a dome behind which said optical head and said illumination source are located; and
   a heating element for cauterizing a tissue within the body lumen, wherein said heating element is shaped to conform to the curvature of said dome, and wherein said heating element extends from the device towards the tissue to be cauterized until it comes in contact with said tissue, and wherein said heating element retracts back towards said dome following cauterization of said tissue.

2. The in-vivo device according to claim 1, wherein said device further comprises micro-motor for extending and retracting the heating element.

3. The in-vivo device according to claim 1, wherein said device is a swallowable capsule.

4. The in-vivo device according to claim 1, wherein said heating element is centered within the field of view of the imager.

5. The in-vivo device according to claim 1, wherein said heating element comprises a straight proximal portion and a twisted distal portion, said distal portion comprising a plurality of prongs.

6. The device according to claim 1, wherein said device comprises a magnetic element.

7. The device according to claim 6, wherein said device is surrounded by external magnetic field generators such to interact with said magnetic element in order to produce controlled movement of the device.

8. The device according to claim 7, wherein said device comprises a resonance circuit.

9. The device according to claim 8, wherein said resonance circuit is switched from open to close, in order to pass electrical current through said heating element.

10. The device according to claim 1, wherein said device further comprises a transmitter for transmitting data acquired by the device to external data receiver.

* * * * *